(12) United States Patent
Saylock et al.

(10) Patent No.: US 8,697,116 B2
(45) Date of Patent: Apr. 15, 2014

(54) PET FOOD PRODUCT AND METHOD OF MANUFACTURE

(75) Inventors: Michael J. Saylock, Kansas City, MO (US); Dan K. Dixon, St. Joseph, MO (US)

(73) Assignee: Nestec S.A., Vevey (CH)

( * ) Notice: Subject to any disclaimer, the term of this patent is extended or adjusted under 35 U.S.C. 154(b) by 216 days.

(21) Appl. No.: 12/911,919

(22) Filed: Oct. 26, 2010

(65) Prior Publication Data

US 2011/0039949 A1 Feb. 17, 2011

Related U.S. Application Data

(62) Division of application No. 10/489,949, filed as application No. PCT/EP02/10386 on Sep. 13, 2002, now Pat. No. 7,842,329.

(60) Provisional application No. 60/322,965, filed on Sep. 18, 2001.

(51) Int. Cl.
*A23K 1/17* (2006.01)
*A23K 1/18* (2006.01)

(52) U.S. Cl.
CPC .................................. *A23K 1/1846* (2013.01)
USPC .......................................................... 424/442

(58) Field of Classification Search
None
See application file for complete search history.

(56) References Cited

U.S. PATENT DOCUMENTS

| | | |
|---|---|---|
| 3,930,031 A | 12/1975 | Kealy |
| 4,039,687 A | 8/1977 | Weyn |
| 4,143,171 A | 3/1979 | Buckley et al. |
| 4,211,797 A | 7/1980 | Cante et al. |
| 4,265,913 A | 5/1981 | Eichelburg |
| 4,410,551 A | 10/1983 | Comer |
| 4,643,908 A | 2/1987 | Sawhill |
| 4,781,939 A | 11/1988 | Martin et al. |
| 5,965,797 A | 10/1999 | Blenk et al. |
| 6,379,738 B1 | 4/2002 | Dingman et al. |
| 6,410,079 B2 * | 6/2002 | Cheuk et al. .................. 426/641 |
| 6,596,303 B1 * | 7/2003 | Bui et al. ....................... 424/442 |
| 6,669,975 B1 * | 12/2003 | Abene et al. .................. 426/302 |
| 6,911,224 B1 | 6/2005 | May et al. |
| 2001/0041202 A1 | 11/2001 | Dupont et al. |

FOREIGN PATENT DOCUMENTS

| | | |
|---|---|---|
| DE | 100 09 510 | 9/2001 |
| WO | 99/35917 | 7/1999 |
| WO | 99/48384 | 9/1999 |
| WO | 00/18252 | 3/2000 |
| WO | 00/53031 | 9/2000 |
| WO | 01/70045 | 2/2001 |
| WO | 01/47371 | 7/2001 |

OTHER PUBLICATIONS

"Colloid" Wikipedia (retrieved online on Aug. 21, 2012; http://en.wikipedia.org/wiki/Colloid) pp. 1-3.*
"Blood meal" Wikipedia (retrieved online on Aug. 21, 2012; http://en.wikipedia.org/wiki/Blood_meal) pp. 1-2.*
"High Fructose Corn Syrup" Wikipedia (retrieved online on Aug. 21, 2012; http://en.wikipedia.org/wiki/High-fructose_corn_syrup) pp. 1-2.*

\* cited by examiner

*Primary Examiner* — Bethany Barham
(74) *Attorney, Agent, or Firm* — K&L Gates LLP

(57) ABSTRACT

A pet food is provided, comprising a sorbent food body and a fluid carrier comprising a functional ingredient absorbed into the body. The body preferably is relatively moist, having a moisture content for example of from 35% to 60% by weight and firm structure that is resilient under initial biting by a pet animal. Protein content is preferably at least 20% by weight. The sorptivity of the body is increased by depleting the body of a first liquid, for example by causing drying by exposure to a source of dry heat, such as in roasting, grilling, frying and baking. Methods of manufacture are disclosed including providing a sorptive food body, causing the body to take up a carrier fluid containing a functional ingredient and packing the body in suitable packaging. The invention further provides delivery means for delivering a functional ingredient to a pet animal, the delivery means comprising a sorbent food body with the functional ingredient absorbed therein. The functional ingredient may be a nutrient or a pharmaceutical.

20 Claims, No Drawings

PET FOOD PRODUCT AND METHOD OF MANUFACTURE

CROSS REFERENCE TO RELATED APPLICATIONS

This application is a divisional of U.S. application Ser. No. 10/489,949, filed Mar. 18, 2004, which is a U.S. National Phase of PCT/EP02/10386 that was filed on Sep. 13, 2002, which claims priority to U.S. Provisional Application No. 60/322,965 filed on Sep. 18, 2001 the content of which is expressly incorporated herein by reference thereto.

BACKGROUND OF THE INVENTION

This invention relates to a nutritionally balanced pet food having an enhanced caloric content and which simulates the appearance of meat. The invention also relates to the moisture-reduced food product and to a process of producing the said product.

Meat emulsion and extrusion products, based on meat protein can be produced by conventional procedures to be in the form of a uniform, homogeneous mass. These do, however, lack sufficient resemblance in respect of structure, texture and appearance to chunks of natural meat.

One attempt to improve such meat products is disclosed in U.S. Pat. No. 4,781,939. This patent discloses processing a meat emulsion under conditions which result in the production of a layered, non-expanded product in the form of chunks or pieces which simulate natural meat chunks in texture, appearance, and consistency. The meat emulsion product is in the form of distinct chunks or pieces having a plurality of juxtaposed, manually separable meat-like layers resembling a chunk of natural meat in appearance, texture, and consistency. The meat emulsion chunks are suitable for use as a partial or complete replacement for more expensive natural meat chunks in both human foods and animal foods. They retain their integrity and shape when subjected to commercial canning and sterilization procedures such as those required in the production of canned, high moisture content foods.

Pet treats differ from normal pet foods in that they are not intended to supply the pet's main ration. Instead, they generally intended as a means of rewarding a peg particularly as part of a process to modify behavior. Therefore, while pet treats may contain certain essential nutrients, they are usually not nutritionally balanced. It is desirable though, that they be highly palatable to pets.

Pet treats are available in different forms. A first category is the dried pet treat, which contains less than about 15% by weight moisture. Examples include baked products, such as bone shaped products for dogs. A second category the semi-moist or intermediate moisture pet treat which has a moisture contents of about 20% to 50% by weight. These products are generally characterized by a soft, crumbly texture and densities comparable to meat or leathery products. These products are usually rendered stable by the inclusion of various acids and solutes which alter the pH and water activity to a level which prevents mold and bacterial growth. A third category covers pet chews and jerkies. These products are chewy, have low to intermediate moisture contents, are relatively dense and are shelf stable. These products are primarily intended to be chewed by the pets and are generally suited for use as treats rather than as complete meals.

There remains, however, a need for a chewy pet food that is can be produced in variants suitable for dogs and cats respectively and without the need for highly specialised processing. It should further have good visual appeal, be highly palatable and structured to encourage chewing, while desirably also providing a complete meal.

It would also be desirable to provide a pet food that functions as a delivery system for a pharmaceutical, a nutritional agent or other functional ingredient, while providing a highly palatable food.

Advantageously, the present invention seeks to address this need.

SUMMARY OF THE INVENTION

Accordingly, the present invention provides delivery means for delivering a functional ingredient to a pet animal, the delivery means comprising a sorbent food body and a functional ingredient absorbed therein.

In an embodiment, the functional ingredient is selected from the group consisting of pharmaceutical, nutritional and calorie boosting agents. The functional ingredient is preferably absorbed in sufficient quantity to be efficacious in treating a condition attributable to the deficiency thereof in a pet animal consuming it.

In an embodiment, the functional ingredient is sorbed in a fluid carrier. Preferably, at least a portion of the fluid carrier is retained in the food body.

In an embodiment, the food body has a moisture content of about 30% to about 60% by weight.

In an embodiment, the absorbed fluid carrier comprises from about 10% to about 60% of the weight of the body after sorption.

In an embodiment, the food body has a caloric density of at least about 1.7 kcal/g. Preferably, the food body has a caloric density of about 1.9 kcal/g to 3 kcal/g.

According to a second aspect of the invention, a method of delivering a functional ingredient to a pet animal comprises forming a sorbent pet food body, providing a fluid carrier containing a functional ingredient and causing the fluid carrier to be taken up at least partially into the food body to provide a desired concentration of the functional ingredient therein. Thereafter, the method may further include packaging said body in a sealed container and providing directions on the container for feeding said body to a pet animal.

In an embodiment, the method includes increasing the sorption capacity of the food body before the fluid carrier is taken up into it. This step may comprise depleting the body of a first fluid and replenishing the fluid-depleted body with a second fluid containing the functional ingredient. In an embodiment the step of depleting the body comprises reducing the moisture content of the body prior to taking up the fluid carrier. In a preferred embodiment, the moisture content is reduced to 40% or less by weight, further preferably to the range from about 25% to 30% by weight.

According to a third aspect of the invention, a pet food comprises an edible body comprising thermally denatured protein and having a caloric density of at least about 1.5 kcal/g, preferably in the range from 1.7 to about 2.8 kcal/g.

In an embodiment, the pet food has a moisture content of about 30% to about 60% by weight. In a preferred embodiment, the moisture content is from about 45% to about 60% by weight.

An another embodiment, the pet food body has substantially varied surface coloration. The coloration includes contrasting darker and lighter areas. In a particularly preferred embodiment, the darker areas appear blackened.

In a further embodiment, the surface coloration is at least partly attributable to a browning reaction.

In a preferred form of the invention, the pet food body is capable of exuding a fatty substance when subjected to light pressure.

In a still further embodiment, the pet food body has a layered structure. The structure may comprise interior and exterior zones, the exterior zone having lower moisture content than the interior zone. In a preferred embodiment, the exterior zone comprises an acidic coating.

In a further preferred form of the invention, the pet food body comprises from about 20% to about 40% protein by weight.

According to a fourth aspect of the invention, a pet food product comprises a food body containing a functional ingredient, such ingredient having been taken up into the body by absorption of a liquid carrier comprising it.

In a preferred form of the invention, the food body has moisture content from about 30% to 60% by weight, further preferably from 45% to 60% by weight.

In an embodiment, the pet food body has a caloric density of at least about 1.5 kcal/g. Preferably, the caloric density is in the range from about 1.6 kcal/g to 3 kcal/g and further preferably, in the range from about 1.9 to 2.8 kcal/g.

Further, in another aspect of the invention, there is provided use of a sorbent edible body in the manufacture of a pet food product, the body having a moisture content of from about 20% to 40% before sorption of a fluid carrier containing a functional ingredient. In a preferred form of the invention, the functional ingredient is selected from the group consisting of pharmaceutical, nutritional and calorie-boosting agents.

According to another aspect of the invention, a pet food product comprises a sealed container, a plurality of edible, formulated, protein rich bodies within the container, said bodies having a browned appearance, a moisture content of from about 30% to about 60% by weight, a caloric density of from about 1.8 to about 2.8 kcal/g and a resilient texture.

In an embodiment, the browned appearance is produced by exposure of the body to a source of dry heat. The browned appearance is preferably discontinuous and non-uniform.

In a further embodiment, the pet food product contains no added water or gravy.

A still further aspect of the invention provides a pet food product comprising a plurality of edible, formulated, protein rich bodies having a browned appearance, a moisture content of 45% to 60% by weight, the moisture having been reduced by exposure of the body to a source of dry heat, protein content of 20% to 40% by weight and caloric density of from 1.9 kcal/g to 2.8 kcal/g and a structure providing firmness of texture to be resilient under initial pressure of biting by a pet animal.

The invention provides further for a pet food comprising an edible meat-like body and a sorbed calorie-dense substance, said substance having a greater caloric density than the said body.

In an embodiment, the meat-like body has a caloric density of at least about 1.5 kcal/g.

According to a still further aspect of the invention, a process for increasing the caloric density of a pet food, comprises forming a pet food body having a first, relatively low, caloric density, providing a fluid comprising an edible substance having a second, relatively high caloric density and causing the fluid to be sorbed into the body so that the substance is retained therein for eating by a pet animal.

The process may include the step of increasing the sorptivity of the pet food body.

This step may be achieved by removing moisture from the pet food body. In a preferred embodiment, the step of removing moisture is accomplished by exposing the body to dry heat. Preferably, the moisture is reduced to the range 20 to 40% by weight.

In an embodiment, a pet food product of the said process is provided, comprising a partly dried edible body having a sorbed liquid substance, a moisture content from about 40% to 60% by mass and a caloric density in the range from about 1.7 to 2.8 kcal/g.

According to a further aspect of the invention, a process for producing a pet food comprises the steps of forming a coherent protein-rich body of food, increasing its sorptivity by removing moisture from the body to a moisture range from about 20% and 40% by weight and replacing at least a portion of the removed moisture with a fluid carrier. Preferably, the fluid carrier contains a functional ingredient. The functional ingredient may be a caloric enhancer. Alternatively, or in addition, the functional ingredient may be a nutrition enhancer such as a dietary supplement or a prophylactic. The functional ingredient may alternatively or in addition be selected from pharmaceuticals.

In a further aspect of the invention, there is provided a pet food product having a moisture content from about 40% to 65% by mass and a caloric density in the range from about 1.7 to 2.8 kcal/g and comprising a partly dried edible body having an absorbed liquid substance. In an embodiment, the liquid substance is a hydrocolloid syrup.

In an embodiment, the pet food comprises a plurality of chunks. Preferably, the mass ratio of chunks to syrup is in the range from about 0.8:1.0 to about 1.3:1.0.

According to another aspect of the invention, a delivery means for delivering a nutritional agent to a pet animal comprises a food body having sorbed therein a nutritional agent. The nutritional agent is preferably sorbed in sufficient quantity to be beneficially efficacious in preventing a condition attributable to the deficiency thereof in such animal.

Further, according to the invention, a method of providing a pet food of enhanced caloric density comprises the steps of providing a pet food body, reducing its moisture content and replacing at least some of the lost moisture with a substance of greater caloric density than the caloric density of the mass prior to having its moisture content reduced. The substance is preferably replaced while in fluid form. The fluid is preferably a liquid. The liquid may include a functional ingredient. The functional ingredient may be a mineral, a vitamin, an extract of a derivative, a metabolite or a prebiotic.

A further aspect of the invention provides a method of delivering at least one ingredient selected from the group consisting of nutritional, functional and pharmaceutical compounds to a pet animal, the method including the steps of providing a pet food body having such ingredient incorporated into the said body after formation thereof, incorporation being by means of an absorbed fluid carrier.

Still further, according to the invention, a pet food product comprises a sealed container containing a moisture-reduced food body and a fluid carrier separately packaged for addition to the food body, the fluid carrier containing a functional ingredient.

Additional features and advantages of the present invention are described in, and will be apparent from, the following Detailed Description of the Invention and the figures.

DETAILED DESCRIPTION OF THE INVENTION

This invention relates to a moist pet food that provides a delivery system for delivering a functional ingredient to the pet animal that eats it. In preferred embodiments, it emulates natural meat in appearance, texture, taste and flavour. The food may thus be manufactured from starting materials that include real meat and meat by-products and be given the appearance of meat that has undergone some form of cooking in a moisture-reducing environment. However, a meat free embodiment is also envisaged, where meat free means having less than 1% of protein derived from animal carcasses sources.

Broadly, in one embodiment, the process of manufacture includes forming a food body having sorptive capacity for taking up a carrier fluid bearing a functional ingredient and causing such carrier fluid to be taken up by the body before packing the thus loaded body in a suitable container. Sorptive capacity may be increased by reducing moisture content of the body and then adding the fluid carrier containing a preselected functional ingredient.

In an alternative embodiment, the process of manufacture includes forming the food body, increasing its sorptive capacity and causing it to take up a fluid carrier comprising a functional ingredient. The body, thus loaded with the functional ingredient, may then be suitably packaged. The sorptive capacity may be suitably increased by depleting the body of a liquid already contained in it.

These process embodiments enable a food body of superior dietary benefit to be provided. The dietary benefit may for example be related to having enhanced caloric density, i.e. a greater number of calories provided per unit volume of chunk than previously, meaning that the pet needs to consume a lower volume of food in order to derive the same caloric benefit as from a food of lower caloric density but higher volume. The pet may therefore feel satiated on a lower volume of food. Its stool volume may consequently decrease.

An advantage of such a food product is that a smaller packaging volume is required per meal ration or serving. Thus, in an embodiment of the invention, the functional ingredient is a substance of high caloric value, greater than the caloric value of the unenhanced food body. By removing low caloric moisture, sorptive capacity is created for taking up a higher caloric substance.

This invention also provides a way of delivering a functional ingredient to a pet animal consumer, in the case where the added carrier contains such ingredient that is taken up into the food body to be retained there until eaten.

For purposes of this specification, the term "functional ingredient" is intended to include, any ingredient that may have or is intended to have a beneficial function in respect of the well-being of the pet animal receiving it. This beneficial function includes a prophylactic effect in respect of dietary deficiency of the functional ingredient concerned. The functional ingredient may therefore be a vitamin, a mineral, an antioxidant, a prebiotic, a micro-organism, for example a probiotic, a moiety such as a metabolite or a supernatant of culture of such micro-organism, an extract from a plant that may contain any of the above, any other suitable health promoting ingredient, a dietary supplement containing any of the above, appropriate combinations and mixtures of the above, and the like. In preferred embodiments, the functional ingredient is selected to be included in a predetermined amount to provide efficacy in preventing or relieving a known health disorder. It will be appreciated that for therapeutic dietary purposes, the carrier fluid may include a medicament.

In preferred embodiments, the pet food product is a coherent food body. As such, the food body is moist but not wet, having had its moisture content reduced to enhance its sorptive capacity. It has a firm, yet resilient structure. In its dried state after moisture reduction, it is capable of taking up a fluid, especially a liquid substance by absorption, in a substantial amount. However, although it may be provided as a final product in this moisture-reduced form, in which it is a sorptive body having capacity for fluid take-up, it is preferably provided as a final product in fluid-enriched form—that is to say already containing a sorbed fluid carrier. Nevertheless, it is within the scope of this invention to provide a moisture-reduced food body separately from the fluid carrier which may later be added.

Where the fluid to be added is a liquid or a liquifiable substance, the final product is preferably capable of visibly exuding a small amount of liquid when lightly pressed or bitten. Preferably the sorption equilibrium is such that visible pooling of fluid does not occur under compression. This sets the product of the invention apart from prior art chunk-and-gravy products.

It is contemplated that, without departing from the essence of the invention, the liquid substance, once added into the food body, may be allowed to solidify so as to exist in solidified form therein under certain temperature conditions. This would be the case where the liquid carrier is a lipid having a melting point above normal room temperature. It can, however, also be provided with a lipid having a melting point below room temperature for storage in refrigerated form for optional later heating just prior to serving.

It is found that the texture provided by the structure of the food body after moisture reduction encourages chewing, rather than immediate swallowing by an animal to which it is administered in use. This chewability of the mass enables more efficient release into the mouth of the functional ingredient contained within the liquid that has infiltrated for sorption into the food body structure. These ingredients may therefore be acted on by the animal's saliva and improve ultimate sorption into the animal's system.

The surface and the interior region of the food body proximate to it is resilient and bitable, in the sense that a pet animal may sink its teeth into it without necessarily immediately penetrating it or causing the mass to disintegrate. The surface and adjoining region is thus resilient under initial pressure of biting, although it will yield to be parted and give access to the interior of the mass under repeated biting or sustained biting pressure.

The surface of the food body is preferably non-uniform in appearance. It may desirably exhibit some effect of browning, searing or charring. This effect may be heat induced, but may also be the result of a chemical reaction such as a browning reaction, for example a Maillard reaction.

The food body is produced from a thermally gellable protein source, preferably mixed with a starch source, the mixture being caused to gel thermally into a food mass. The mass may, after forming, be divided into a plurality of separate food bodies. These separated bodies will be referred to as chunks.

The food mass, or chunks thereof, are subjected to a moisture reduction step. In a preferred embodiment, the moisture reduction is achieved in a thermal treatment step, such as by way of exposure to a source of dry heat. This moisture reduction step provides the mass with capacity to undergo sorption of the carrier fluid, such as the liquid, containing the functional component. Preferably, where the carrier is a liquid, the added liquid is different from the one removed. An example of such a liquid is a lipid containing a calorie-rich gravy formulation. It may also be a hydrocolloid or gum-based solution or be aqueous. For example, a suitable hydrocolloid syrup may contain up to about 90-98% water, the balance comprising xanthan gum, sugar(s), flavorants, amino acids, antioxidants, vitamins and from about 1-9% lipids by weight.

The carrier fluid may be a gas. In this case it is preferably selected from a gas that is compatible with the food body components, preferably being inert. However, it may be a gas that reacts with selected components in the food body to enhance flavor or neutralise undesirable flavor constituents. Suitable examples of relatively inert carrier gases are nitrogen and carbon dioxide.

By providing a carrier fluid with a functional component in this way, additional components are be added to the mass after the forming stage. This is advantageous where it is desired to include in the mass a component that is known to be sensitive to heat or other conditions associated with the forming stage, or other earlier treatment steps.

The food mass or chunks thereof are contacted with the fluid in a manner effective to cause sorption of the fluid therein. In the case of a liquid, a preferred method of causing contact includes preparing a bath of the liquid and causing the food mass in chunk form to pass through the bath. Alternative methods may include spraying, such as in a fluidized bed arrangement, or through a spray chamber or tunnel for a time sufficient for a desired level or sorption to occur. These latter methods may be suitably adapted for sorption of the carrier fluid when in gaseous form.

In the case where the carrier fluid contains a calorie enhancer, the body, desirably after sorption thereof, has a caloric density of at least about 1.5 kcal/g. Preferably it is in the range from 1.7 kcal/g to 2.8 kcal/g and most preferably from 1.9 to 2.7 kcal/g. The food bodies of the final product preferably comprise from about 40% to 90% solid chunk material and about 60% to 10% absorbed fluid, by mass.

After fluid sorption, the food chunks may further be coated or subjected to other treatment steps, if desirable, prior to being packaged. At packaging, a plurality of the chunks may be charged into a sealable container. In an embodiment, the chunks are mixed with food pieces of differing texture, for example softer, less chewy pieces, or pieces made from entirely different, but preferably complementary foodstuffs. An example is a conventional wet food chunk. Additionally or alternatively, the chunks can be mixed in with harder, dryer food pieces, such as kibbles or biscuits. In an embodiment, they can be co-packaged in a single container with drier or wetter food pieces, each respective food type being sealed in a separate compartment. The compartments may desirably be hermetically isolated from each other to prevent moisture migration from one to the other. The dried, sorptive chunks may also be packaged to be separately sealed from a quantity of the fluid carrier, allowing for subsequent combination, for example at feeding time, by breaking of the separating seals by the pet minder. The fluid carrier may contain the functional ingredient, or may have it provided in a separate sealed container or compartment in a container for mixing prior to being added to the dried sorptive food chunk.

The food body of the invention, in final product form, for example as a chunk, preferably has a moisture content of in the range from about 30% to 60% by weight. Further preferably the moisture content is in the range from about 45% to 60% by weight. In this form, the body or piece is suitable for feeding to a cat or a dog, depending respectively on the final product make-up with regard to considerations such as palatability and chunk size, as will be appreciated by the person skilled in the art.

The food body itself comprises protein, starch and other ingredients, obtainable from any suitable source, the choice thereof being largely determined by nutritional needs, palatability considerations, and final form of food to be produced.

The protein source may be a vegetable protein source, an animal protein source, or a mixture of these protein sources. Suitable vegetable protein sources are gluten, wheat protein, soy protein, rice protein, corn protein, and the like. These proteins may be provided in the form of flours, concentrates and isolates as desired. Animal proteins are however preferred. Suitable animal protein sources are muscular or skeletal meat of mammals, poultry, and fish; meals such as meat meal, bone meal, fishmeal, and poultry meal; by-products such as hearts, liver, kidneys, tongue and the like; and milk proteins. The body contains protein in an amount of at least about 20%, but preferably no more than about 45% by weight. In a further preferred embodiment, the protein content is from 25 to 35% by weight.

The starch source is conveniently a grain such as corn, rice, wheat, barley, oats, or soy, and mixtures of these grains. The grain is conveniently provided in the form of a flour. Pure or substantially pure starches may also be used if desired. If flours are used, they will also provide some protein. Hence it is possible to use a material which is both a protein source and a starch source.

Various other ingredients, for example, salt, spices, seasonings, vitamins, minerals, flavoring agents, lipids and the like may also be incorporated into the thermally gellable mixture as desired. If added, the lipids may be any suitable animal fats; for example tallow, or may be vegetable fats.

A plasticizing or water controlling agent may be added to the protein source comprising the initial pre-chunk formulation; so as to soften the texture of the eventual final product, by promoting retention of at least some of the available water. Any suitable plasticizing or water controlling agent may be used. Suitable examples include for example, hydrogenated corn syrup, glycerin, propylene glycol, butylene glycol, polyhydric alcohols such as glycerol and sorbitol. Suitable sugars include invert sugar, and sucrose. Suitable salts include sodium chloride and sodium pyrophosphates.

The thermally gelled protein-rich mass may be produced in many different ways as desired.

For example, a thermally gellable mixture may be prepared from water, protein and all the other ingredients to be included in the moisture-reduced, formulated food product. The thermally gellable mixture is then heated and formed into layers. This may be done as described in U.S. Pat. Nos. 4,781,939 and 5,132,137; the disclosures of which are incorporated by reference. As described in these patents, the thermally gellable mixture is fed to an emulsion mill in which the mixture is subjected to rapid mechanical heating and shearing. Any suitable emulsion mill may be used, for example the emulsion mill disclosed in U.S. Pat. No. 5,132,137. Other suitable emulsion mills are commercially available under the trade name of Trigonal and may be obtained from Siefer Maschinenfabrik GmbH & Co KG, Bahnhofstrasse 114, Postfach 101008, Velbert 1, Germany.

In the emulsion mill, the temperature of the mixture is raised to the desired gelling temperature within a very short time; usually less than one or two seconds. Preferably the temperature is raised to about 100° C. to about 120° C. Alternatively, the temperature may be raised to in the range of about 45° C. to about 75° C. as described in U.S. Pat. No. 5,132,137. Usually the mechanical energy generated in the emulsion mill will be sufficient to heat the mixture to the desired temperature but this may be supplemented by the injection of superheated steam.

The heated mixture is ejected from the emulsion mill in a thin stream into a holding tube. Because the heat mixture enters the holding tube in a thin stream, it forms thin layers upon heated mixture already in the holding tube. The layered, heated mixture in the holding tube then gels while moving slowly along the holding tube. Each layer of the layered, heated mixture remains substantially, visually distinct. The residence time of the heated mixture in the holding tube is sufficient for the mixture to gel into a firm, gelled product mass upon reaching the exit of the holding tube. At this stage, the gelled mass has a moisture content generally in the range from about 50% to about 70% by mass. It also preferably has the highly striated appearance and the texture of meat.

Alternatively, by way of example, the thermally gelled mass may be produced by emulsifying water, protein and lipids and the ingredients to be included in the moisture-reduced, formulated food product. A high speed emulsifier or homogenizer is particularly suitable for emulsification. If necessary or desired, a gelling agent may be added. The emulsion is then heated to thermally gel the emulsion to provide a thermally gelled mass; for example in a mixer-cooker, steam oven or extruder. The thermally gelled mass may then be forced through an orifice such as an extrusion die to provide a gelled product suitable for cutting into pieces. Again, moisture content will generally be in the range from about 50% to about 70% by mass.

The gelled product mass, obtained from whichever of the alternative and non-limiting exemplary processes above is used, may then be divided into pieces before moisture is removed. However, moisture may alternatively or in addition be removed before the mass is divided into chunks. Division is preferably by means of a suitable cutter. The pieces are cut to a size suitable for feeding to pets as part of a pet food meal; for example having a minimum dimension of about 8 mm. The pieces may then be screened to remove fines.

The pieces may alternatively be cut or otherwise formed into shapes suitable for feeding to a pet as a treat. The sizes of such pieces would tend to be larger than those used for making up a complete pet food meal.

The coherent, protein-rich pieces thus formed are then subjected to a texturisation step. This step serves to increase sorptivity. Typically, it includes removing moisture from the pieces. A source of intense, dry heat is preferred. Depending on the intensity of the heat, time of exposure and moisture content of the pieces, this may result in a body acquiring a structure comprising at least two zones—an outer or exterior zone of lower moisture content than an interior zone of higher moisture content.

Moisture removal may be accomplished by the drying the food mass, or chunks thereof, in a conventional dryer. Preferably they are dried in a state of relative movement with air, such as a stream of hot air, or by causing them to fall through heated air. A preferred example of a dry heat process is convection drying. The air temperature in the dryer should be suitable to accomplish rapid reduction of moisture to the range from about 20% to about 40%—preferably from about 25% to about 30% by weight—within a few minutes. A typical drying time and temperature combination is 150° C. to about 200° C.—for example about 160° C. to about 180° C. for 1 to 2 minutes.

The pieces may alternatively, or, in addition, similarly be dried in a high velocity hot air dryer. For a time sufficient to dry them to the desired moisture content. Drying time should not exceed about 10 minutes; and should preferably be less than about seven minutes, more preferably in the range from 4 to 6 minutes. The temperature range is desirably from about 140° C. to 180° C. A preferred set of drying parameters is 140° C. to 160° C. for about 5 to 3 minutes. This has been found to reduce moisture and increase firmness of the body to the desired degree. It will, however, be appreciated that the specific time and temperature needed for any particular product may be determined by a skilled person without undue experimentation. Alternatively, drying may be performed by contacting the food body or pieces thereof with a heated surface.

It is found that the dried bodies produced from layered pieces retain the expanded, layered structure of the undried, layered pieces and, surprisingly, do not noticeably shrink, thus retaining their meat-like appearance.

After moisture removal, the thus at least partially dried and now more sorptive chunks are ready for addition of the functional component via the fluid carrier. Where addition is by way of an aqueous carrier, the desired moisture content after this step is from 30% to 60% but is preferably from 45% to 60% by weight.

The dried pieces may also be coated, for example with flavoring agents. This is done preferably after sorption of the fluid carrier with the functional component. Suitable flavoring agents include digests of animal matter, amino acids such as glycine, fats such as tallow, and the like.

At the coating stage, where implemented, the pH of the pieces is preferably reduced. Typically this is from a pH in the range from 6.0 to 6.5 down to a value in the range 4.0 to 5.5. The pH reduction is accomplished by acidifying the pieces, preferably by applying an acidic coating to them. A food grade acid, for example phosphoric acid, is preferably used. In a preferred embodiment, the coating comprises from about 1% to 5% by weight of the coated food body.

Advantageously, the coating may further comprise a sugar, such as sucrose or glucose, for reaction with the acid to provide a highly palatable seared or browning effect in the coating, enhancing the browning that may already have been produced as a result of the moisture reduction step. However, the sugar may in addition or alternatively be included in the initial protein-rich formulation prior to the gelling stage, or be added at any convenient later stage.

After taking in by absorbing at least some of the carrier fluid and functional component, the pieces are packed into suitable containers, in particular into sealable cans or pouches. Before being sealed, the container headspace is gas flushed with a suitable gas for increasing product storage stability, for example nitrogen or carbon dioxide or non-toxic inert gas. In this form, the replenished dried pieces are particularly suited for feeding to pets as a complete meal or part of a meal. Alternatively, the pieces may be fed as treats. The treats may be fed as snacks between meals, or as rewards. Because of the space-saving advantage of the enhanced caloric density embodiments of this invention, the product is particularly suited for use as pet snacks while travelling or being away from home.

In this embodiment, the pieces are preferably closely packed in the containers and no additional water or other liquid, such as gravy, is added. Once sealed, the containers may be sterilized by retorting. The heat of sterilization promotes reaction of the acid with sugars in or on the food pieces. The result of this reaction is seen in a dark non-uniform surface effect on the pieces, akin to searing or charring.

In an alternative embodiment, the pieces, after being dried to reduce moisture and then cooled, are packed into containers, whereafter the carrier liquid is added for at least partial sorption and at least partial replacement of the moisture lost in drying. As mentioned previously, in another embodiment, the partially dried chunks may be packed without carrier fluid added, the latter being packaged in a separate container or in a suitably isolated compartment of the same container as the chunks. The chunks and fluid may be combined at point of use.

Thus, in preferred embodiments of the invention, the final product pieces preferably comprise about 10% or less by weight of starch; about 20% to about 45% by weight of protein; about 5% to about 15% by weight of lipid; and about 45% to about 60% by weight of moisture, wherein the moisture is contributed by the original residual moisture and replaced moisture from the carrier fluid. If additional ingredients—in addition to the coating components discussed above—such as salts, sugars, spices, seasonings, flavoring agents, minerals, and the like are included in the pieces, these additional ingredients preferably make up about 0.5% to about 15% by weight of the pieces.

In the case of medium to large dogs, it is found that the chunks should preferably be within the following size limits: shortest lateral dimension from 8 mm to 12 mm and longest from 16 mm to about 25 mm. Although the chunk may indeed be generally rounded, it is found generally that bodies of more blocky proportions are preferable, as these appear to encourage more chewing and can therefore be expected to have a better effect on oral health. However, not only blocky and rounded shapes, but also shapes comprising combinations thereof in the same container are within the scope of this invention.

Through the process of this invention, there is thus advantageously provided a moist pet food having a caloric density significantly higher than commercial wet pet food, thereby supplying more nutrition per unit weight than previously found. Furthermore, because of the lower water content that is achievable, the product carries less weight and allows savings in packaging material.

It will be appreciated that numerous modifications and variations may be made to the embodiments described above without departing from the spirit and scope of the invention. Of course, particular flavors used will differ depending upon the type of animal intended to consume the food product.

Example 1

A base mix for producing a thermally gellable mixture is prepared from meat protein, wheat gluten, de-fatted soy flour, other ingredients and water in the following approximate proportions by weight:
  69.0% Meats
  19.0% Wheat
  5.0% Soy Flour
  4.0% Water
  3.0% Other (minerals, sugars, vitamins, flavors, etc.)

The thermally gellable mixture is run through an emulsion mill (a Trigonal Mill obtained from Siefer Machinenfabrik GmbH & Co KG). The mixture leaves the emulsion mill heated to a temperature of about 112° C. and is discharged into a holding tube. The residence time in the holding tube is about 3 minutes. The product leaving the holding tube is in a gelled form and is cut into pieces about 8 mm in length. The pieces have a striated, meat-like appearance.

The pieces are sieved to remove fines. The moisture content of the pieces is found to be about 55% by weight. The pieces are then transferred to a convection dryer in which they are exposed to intense dry heat of 180° C. for about 4 minutes to reduce their moisture content. The pieces are then removed and cooled to ambient temperature. The dried pieces retain the striated, meat-like appearance and have pH of approximately 6. Blackened patchy areas were visible at the surface.

The composition of the pieces after drying is determined to be as follows (weight %):
  39% protein
  20% fat
  27% moisture
  5% ash
  9% sugars (mainly sucrose), other carbohydrates and conventional other ingredients.

The dried pieces are then transferred to a re-fluidizing apparatus for blending with a hydrocolloid-containing gum-based solution in the form of a slurry. The ratio of the slurry to the semi-dry chunks is approximately 20:80 by weight. The slurry contains about 0.7% guar gum, about 90% water and 5% omega 3 fatty acid by weight as well as conventional colorants, flavorants, reducing sugars to promote browning. In addition it includes 15 mg/1000 kcal beta-carotene and 500 IU/1000 kcal vitamin E. It has a caloric density of about 4.2 kcal/g. The pieces are bathed in the slurry to allow the slurry to infiltrate them. Contact time is about 2 minutes.

Finally, the pieces are packed in to a sealable can. No additional gravy, water or other moisture source is added. The can is sealed and retorted. After allowing it to cool to ambient temperature, the can is opened and the contents examined.

The pieces are observed to have a non-uniform meaty-looking surface of varied coloration. The previously observed blackened patches remain visible. The pieces have a slightly greasy feel and, on being lightly pressed, exude fatty juices. A representative sample from the pieces is analysed for caloric content. The caloric density is found to be 2.5 kcal/g. Moisture content is found to be 44% by weight.

Example 2

Semi-dried pieces made according to the process of example 1 were packed in a retortable pouch container and sealed. The contents were retorted. A lipid based gravy having caloric density of 4.5 kcal/g was sealed in a sachet and fixed to the pouch. The seals of the pouch and sachet were broken and the contents mixed together. The mixture was allowed to stand for a few minutes to allow most of the gravy to be absorbed by the chunks. This provided a pet meal of enhanced caloric value available for feeding to a pet.

Example 3

A base mix for producing a thermally gellable mixture is prepared from meat protein, wheat gluten, de-fatted soy flour, other ingredients and water in the following approximate proportions by weight:
  67% Meats
  18% Wheat
  7% Soy Flour
  5% Water
  3% Other (antioxidants, sugars, vitamins, flavors, etc.)

The thermally gellable mixture is run through an emulsion mill (a Trigonal Mill obtained from Siefer Machinenfabrik GmbH & Co KG). The heated mixture leaves the emulsion mill at a temperature of about 112° C. and is discharged into a holding tube. The residence time in the holding tube is about 5 minutes. The product leaving the holding tube is in a gelled form and is cut into pieces about 8 mm in length. The pieces have a striated, meat-like appearance.

The pieces are sieved to remove fines. The moisture content of the pieces is 60% by weight. The pieces are then transferred to a high velocity, hot air dryer in which they are dried at a temperature of 165° C. for about 6 minutes. The dried pieces puff slightly due to steam release during hot air drying but retain the striated, meat-like appearance and have pH of 6.

The composition of the pieces after drying was determined to be as follows (weight %):
  39% Protein
  8% Starch
  20% Fat
  28% Moisture 2% sugars, in particular sucrose or glucose
2% Other The dried pieces were then passed though a bath containing a lipid-based gravy mix that included 20% of a supernatant of culture of the probiotic *lactobacillus acidophilus*. Residence time in the bath was about 2 minutes.

The pieces were found to have a coating of the gravy mix and a moisture content now of about 34% by weight. The coated pieces retained their firm, yet resilient texture.

Finally, the pieces were packed in to a sealable can without any further gravy or water being added. The can was sealed and retorted. After allowing it to cool to ambient temperature, the can was opened and the contents examined.

The food pieces were observed to have a non-uniform meaty-looking surface of varied coloration. The pieces had a very slight oily feel and, on being lightly pressed, exuded fatty substances. Stronger pressing caused a substantial pool of gravy-like liquid to form around them. A representative sample taken from the pieces was analysed for caloric content. The caloric density was found to be 2.2 kcal/g.

Example 4

Chunks were made as described in example 1 above, and were subjected to moisture reduction in a convection dryer to achieve an intermediate moisture content of 38%. These chunks were then passed through a fluidised bed apparatus where they were contacted with a stream of nitrogen at 35° C. in which were dispersed finely ground ascorbic acid (vitamin C) particles.

The chunks were removed from the reactor and it was determined that they had absorbed ascorbic acid to a level of 20 mg per 100 g. Caloric density was about 2.5 kcal/g. Moisture content was about 30%.

Example 5

Pieces of a pet food having a meat-like appearance were produced from a starting formulation and using the process as described in example 1. However, drying was carried out on a heated steel belt passing through a hot air dryer as described in example 2 and conditions were adjusted to provide final dried pieces with a moisture content of 28% and a seared appearance. In this case, drying time was about 2 minutes with mean dryer temperature at about 200° C. Belt temperature was maintained at 200° C. The dried pieces retained their pre-drying striated, meat-like appearance and had pH of 6. They had a slightly oily feel. Approximate average dimensions of the pieces were length and width 10 mm and depth 20 mm. It was determined that the caloric density of the pieces was 2.9 kcal/g.

Example 6

Pieces were produced from a starting formulation and using the process as described in example 3. However, the drying conditions were adjusted to provide final dried pieces with a moisture content of 23%. In this case, drying time was about 4 minutes with mean dryer temperature at about 177° C. The resultant dried pieces and a very slightly greasy feel and average dimensions of 18 mm by 15 mm by 32 mm. They were packaged in a retortable plastic pouch and a gravy mix containing 95% by weight of a 90:10 water/tallow emulsion and a mixture of vitamins and antioxidants was added. When viewed through the transparent package material the pieces were surrounded by the gravy mix. A week later, little of the gravy mix was visible. When the package was opened and the pieces poured out into a dish, oiliness was visible on the pieces. The moisture content was determined to be 35% by weight. Caloric density was about 2.2 kcal/g.

Example 7

A canned pet food product comprising chunks of layered meat emulsion in an aqueous gravy is prepared by the following procedure.

Blocks of frozen meat are first cut or broken into pieces about 10 cm inches in size and the pieces are ground in conventional meat grinder equipped with a 1 cm plate. The proportions of meat material used are as follows:

| Meat Type | Parts by wt. |
|---|---|
| Mechanically deboned beef | 60 |
| Lungs | 25 |
| Liver | 15 |

The ground meat is introduced into a mixer in which it is heated by steam injection to a temperature of about 0° C. After mixing, the blend of ground meat materials is fed into an emulsion mill in which the meat is cut and sheared to form a meat emulsion which is heated by mechanical working during emulsification to a temperature of about 35° C. The warm meat emulsion is pumped from the emulsion mill into a continuous mixer where it is thoroughly admixed with a blend of dry ingredients containing the dry proteinaceous materials, wheat gluten and soy flour together with vitamins, minerals and spices to form a thickened, viscous meat emulsion containing about 80% meat material, 19% dry proteinaceous material, and the balance vitamins, minerals and spices. The viscous meat emulsion thus formed is pumped from the continuous mixer into a vacuum-stuffer to deaerate the emulsion.

After deaeration, the viscous emulsion, which is at a temperature of about 37° C., is pumped into an emulsion mill in which the emulsion is cut and sheared under conditions to increase the fineness of the emulsion and almost simultaneously heat the emulsion to about 110° C. At this temperature, protein coagulation proceeds rapidly, so that a firm meat emulsion product is formed within about 2 minutes.

The hot emulsion is pumped directly from the emulsion mill into an elongated tube having an internal diameter of about 6 cm and a length of about 6 m. The flow rate of the emulsion through the tube is controlled to provide the emulsion with a residence time of about 2 minutes in the tube.

Steam, at a pressure of between 0.5-1.0 kg/cm$^2$, is injected into the emulsion at a point within the first 25% of the length of the tube, with the steam being injected at 60 second intervals for a period of about 3 seconds per injection. A firm emulsion product is intermittently discharged from the elongated tube in the form of discrete irregularly shaped meat-like pieces or chunks varying in length from about 1.25 cm to about 5 cm or more, with each of the chunks having a plurality of juxtaposed layers of set meat emulsion bonded together and resembling natural meat chunks in appearance and texture. The distinct layers of the chunks, while being bonded together are manually separable, similar to cutting along the grain of a chunk of meat. The individual chunks discharged from the tube are at a temperature of about 99° C.

The chunks are then dried by convection, using a hot air, impingement dryer, so that the chunk moisture is reduced from about 50%-52% by weight at the tube discharge end to about 27%-28% by weight. Dryer temperatures were in the range of about 140° C.-160° C. and residence time was about 3½ minutes. These chunks are filled into suitable flexible pouch-type packaging. A hydrocolloid syrup is then added. The ratio of chunks to syrup is about 1.15:1.0 by weight. The syrup is made up of about 98% water with the remainder comprising xanthan gum, sugars, meaty flavorants (i.e. tuna, salmon, liver, poultry hearts/liver, etc.), amino acids, antioxidants, vitamins, fats/oils, etc. Gas-flushing of the headspace with a nitrogen/carbon dioxide mixture is also used to increase storage stability. The resultant product is retorted according to conventional thermal process specifications. The finished composition is as follows (by weight):

22% protein
10% fat
60% moisture
3% ash
5% carbohydrate

The chunks were found to have a caloric density of about 1.8 Kcal/g.

Example 8

Chunks made as in example 7 above are size-reduced to flakes and dried in a convection drier to a moisture content of about 25%. This dried component is blended at a 1.3:1.0 ratio with a hydrocolloid based syrup. This syrup contains 98% water, with the remainder comprising xanthan gum, sugar(s), amino acids, colorants, antioxidants, and B-vitamins.

Once uniform, a third component, consisting of a combination of ground poultry and poultry by-products, fish and fish offal, is added and blended to provide a finished composition of:

40% Dried chunks/slices, etc.
30% Syrup
30% Ground poultry and fish by-products, etc.

This mixture is filled into pouches that are heat-sterilizable and sterilized. Finished composition is as follows:

20% Protein
10% Fat
60% Moisture
3% Ash
7% Carbohydrate

The mixture is removed from the can and analysed for caloric content. The mean caloric density is determined at 1.9 kcal/g.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method of delivering a functional ingredient to a companion animal, the method comprising:
   depleting a food body of a first fluid to form a fluid-depleted food body by exposing the food body to drying conditions selected from the group consisting of 1) a temperature from 150° C. to 200° C. for 1 to 2 minutes and 2) a temperature from 140° C. to 160° C. for 3 to 5 minutes;
   replenishing the fluid-depleted food body with a second fluid that is a fluid carrier containing the functional ingredient, to form a replenished food body, the fluid carrier comprising a fluid selected from the group consisting of a lipid, a hydrocolloid and a gas; and
   forming a pet food comprising the fluid-replenished food body and the functional ingredient absorbed therein.

2. The method of claim 1 wherein the functional ingredient is selected from the group consisting of a vitamin, a mineral, an antioxidant, a prebiotic, a probiotic, a plant extract, a pharmaceutical agent, a nutritional agent, a calorie boosting agent and mixtures thereof.

3. The method of claim 1 wherein the functional ingredient is present in the replenished food body in sufficient quantity to be efficacious in treating a condition attributable to a dietary deficiency in the companion animal consuming said ingredient.

4. The method of claim 1 wherein the fluid-replenished food body has a moisture content of about 30% to about 60% by weight.

5. The method of claim 1 wherein the fluid-replenished food body comprises from about 20% to about 40% protein by weight and a moisture content from about 30% to about 60% by weight and has a caloric density from about 1.0 kcal/gram to about 3 kcal/gram.

6. The method of claim 1 wherein the companion animal is selected from the group consisting of a dog and a cat.

7. The method of claim 1 wherein a moisture content of the food body is reduced prior to uptake of the fluid carrier.

8. The method of claim 7 wherein depleting the food body of the first fluid reduces a moisture content of the food body to 40% or less by weight.

9. The method of claim 1 wherein the fluid-replenished food body has a moisture content of about 45% to about 60% by weight.

10. The method of claim 1 wherein the pet food contains no water or gravy added to the fluid-replenished food body.

11. A method of delivering a functional ingredient to a companion animal, the method comprising:
   reducing a moisture content of a food body by exposing the food body to drying conditions selected from the group consisting of 1) a temperature from 150° C. to 200° C. for 1 to 2 minutes and 2) a temperature from 140° C. to 160° C. for 3 to 5 minutes;
   contacting the food body having reduced moisture content with a fluid carrier comprising the functional ingredient such that at least a portion of the fluid carrier is taken up by the food body, the fluid carrier comprising a fluid selected from the group consisting of a lipid, a hydrocolloid and a gas; and
   using the food body that has taken up the fluid carrier in a pet food comprising the food body and the functional ingredient absorbed therein.

12. A method of delivering a functional ingredient to a companion animal, the method comprising:
   reducing a moisture content of a pet food body by exposing the food body to drying conditions selected from the group consisting of 1) a temperature from 150° C. to 200° C. for 1 to 2 minutes and 2) a temperature from 140° C. to 160° C. for 3 to 5 minutes; and
   replacing at least some of the lost moisture with a substance of greater caloric density than the caloric density of the food body prior to reduction of the moisture content, and the substance is a fluid comprising the functional ingredient, retained in the food body, and selected from the group consisting of: a lipid, a hydrocolloid and a gas.

13. The method of claim 1 wherein the replenished food body comprises the fluid carrier in an amount from about 10% to about 60% by weight of the replenished food body.

14. The method of claim 1 wherein depleting the sorbent food body of the first fluid reduces moisture content of the food body to 25 to 30% by weight.

15. The method of claim 1 wherein depleting the food body of the first fluid comprises exposing the food body to dry heat.

16. The method of claim 1 comprising forming the food body from a thermally gellable protein source mixed with a starch source before depletion of the first fluid.

17. The method of claim 16 wherein the protein source is 25 to 35% by weight of the food body.

18. The method of claim 1 wherein the second liquid is different type of liquid than the first liquid.

19. The method of claim 1 wherein the food body has a moisture content of about 50% to about 70% before depletion of the first fluid.

20. The method of claim 1 wherein depleting the food body of the first fluid comprises a heat treatment selected from the group consisting of convection drying, drying in a high velocity hot air dryer, and a combination thereof.

* * * * *